United States Patent [19]

Milstein et al.

[11] Patent Number: 5,126,492
[45] Date of Patent: Jun. 30, 1992

[54] PRODUCTION OF AROMATIC ALDEHYDES

[75] Inventors: David Milstein, Rehovot; Yehoshua Ben-David, Givataim, both of Israel

[73] Assignee: Yeda Research and Development Co. Ltd., Rehoyot, Israel

[21] Appl. No.: 546,316

[22] Filed: Jul. 2, 1990

[30] Foreign Application Priority Data

Jul. 5, 1989 [IL] Israel ................................. 090881

[51] Int. Cl.$^5$ ........................ C07C 45/42; C07C 45/49
[52] U.S. Cl. .................................. 568/437; 568/428; 556/13; 556/18
[58] Field of Search ................. 568/428, 437, 426; 556/13, 18

[56] References Cited

U.S. PATENT DOCUMENTS

| 3,642,658 | 12/1968 | Allum et al. | 556/18 |
|---|---|---|---|
| 4,331,818 | 5/1982 | Riley | 556/18 |
| 4,397,787 | 8/1983 | Riley | 556/18 |
| 4,605,749 | 8/1986 | Buchman et al. | 568/428 |

FOREIGN PATENT DOCUMENTS

| 0109606 | 8/1983 | European Pat. Off. | 568/428 |
|---|---|---|---|
| 0352166 | 1/1990 | European Pat. Off. | 568/428 |

OTHER PUBLICATIONS

Huser, M. et al "Chlorocarbon Activation: Catalytic Carbonylation of Dichloromethane and Chlorobenzene", *Angew. Chem. Int. Ed. Engl.* 28 (1989) No. 10, pp. 1386-1388.

Mutin, R. et al "Bi-metallic Activation in Homogeneous Catalysis: Palladium-catalyzed Carbonylation of Tricarbonyl(chloroarene)chromium Complexes to the Correspondidng Aldehydes, Esters, Amides, and α-Oxo Amides", *J. Chem. Soc., Chem. Commun.*, 1988, pp. 896-898.

*Primary Examiner*—Werren B. Lone
*Attorney, Agent, or Firm*—Browdy and Neimark

[57] ABSTRACT

Aromatic aldehydes are produced by catalytic formylation of aryl chlorides in the presence of a palladium chelating phosphine ligand complex of the formula $(R_2R_2P(CH_2)_nPR_3R_4)_2Pd$, wherein n is 3 or 4 and $R_1$ to $r_4$ are H, alkyl, cycloalkyl or aryl, at least one of them being alkyl or cycloalkyl.

20 Claims, No Drawings

PRODUCTION OF AROMATIC ALDEHYDES

FIELD OF THE INVENTION

The invention relates to a process for the direct production of aromatic aldehydes, starting with aryl chlorides. The process is based on the reaction of aryl chlorides with carbon monoxide and a formate salt in the presence of a catalyst system comprising a palladium complex with a phosphine ligand, the reaction being effected under atmospheric or under mild pressure.

BACKGROUND OF THE INVENTION

Catalytic carbonylation of aryl bromides and iodides to yield aldehydes is reported to take place with $(P\phi_3)PdX_2$ ($\phi$=phenyl, X=halogen) or $PdCl_2$ as catalysts under hydrogen pressure and a base, usually a tertiary amine (Schoenberg A. et al., (1974) J.Am.Chem.Soc., Vol. 96, p. 7761; Yoshida H. et al., Bull.Chem.Soc.Jpn. (1976) Vol. 49, p. 1681; Heck R. F., "Palladium Reagents in Organic Synthesis", Academic Press, New York, (1985) pp.359-361).

It is also possible to convert aryl bromides and iodides to aldehydes in the absence of dihydrogen with palladium $P\phi_3$ complexes as catalysts, by using a hydrogen donor, such as a silyl hydride compound or a formate salt (I. Pri-Bar and O. Buchman, J.Org.Chem. (1984), Vol. 49, p. 4009).

However, the art teaches away from utilization of aryl chlorides in these processes, explicitly stating that these compounds are inert. Indeed, we have also confirmed, in our experiments, the inertness of chlorobenzene with palladium $P\phi_3$ complexes, under conditions that are reported for converting bromo- and iodobenzene to benzaldehyde.

Chloroarene chromium tricarbonyl complexes react with CO and $H_2$ in the presence of a base and $Pd(P\phi_3)_2Cl_2$ as catalyst to yield the corresponding aldehyde (Mutin, R., et al.,(1988) J.Chem.Soc.,Chem.Commun., p.896). However, this reaction utilizes stoichiometric amounts of the chromium complex and it is explicitly stated that free aryl chlorides are not reactive.

A serious limitation of the above synthetic processes, which hinders industrial utilization, is the fact that aryl chlorides which are much more attractive as starting materials than aryl bromides and aryl iodides, are not reactive.

Recently, after the first filing of this patent application on Jul. 5, 1989, Huser et al. described the carbonylation of chlorobenzene with dihydrogen in the presence of the catalyst $Pd(PR_3)_2$, wherein R is isopropyl or cyclohexyl (Huser, M. et al., Angew.Chem.Int.Ed.Engl. (1989) Vol. 28, p.1386).

We have discovered conditions under which it is possible, for the first time, to directly carbonylate aryl chlorides to aldehydes in the absence of hydrogen. When a catalytic amount of a chelating phosphine ligand is used in conjunction with a palladium catalyst, preferably in a polar solvent, aryl chlorides react with CO and a formate salt under mild pressure to yield the corresponding aromatic aldehyde.

SUMMARY OF THE INVENTION

The invention relates to a process for the production of aromatic aldehydes, starting with aryl chlorides. The process involves the formylation of aryl chlorides by reacting same with carbon monoxide and a formate salt under mild pressure in the presence of a catalyst system comprising a complex of a palladium compound with a chelating phosphine ligand. The invention further relates to such palladium chelating phosphine ligand complexes.

The reaction takes place according to the following reaction scheme:

$$ArCl + CO + HCO_2X \rightarrow ArCHO + CO_2 + XCl$$

wherein Ar is a carbocyclic aryl optionally substituted by one or more radicals selected from alkyl, aryl, F, Cl, CN, $OR_6$, $COR_6$, $CO_2R_6$ and $SO_3R_6$, wherein $R_6$ is H, alkyl or aryl and X is a cation, preferably derived from an alkali or alkaline earth metal, e.g., Na, Li, Ca, Mg.

The reaction is advantageously carried out in a solvent that is inert to the reactants and products, preferably a polar solvent, such as dimethylformamide (DMF) or dioxane. The temperature of the reaction is generally between about 100°-250° C., the optimum temperature being about 150° C.

The new, electron-rich, chelate-stabilized complexes of the invention are represented by the following formula $$(R_1R_2P(CH_2)_nPR_3R_4)_2Pd$$

wherein n is 3 or 4 and $R_1$ to $R_4$ are H, cycloalkyl, alkyl or aryl, at least one of them being alkyl or cycloalkyl.

In a preferred embodiment, $R_1$ to $R_4$ are identical alkyl groups, preferably isopropyl. The preferred phosphine ligand is 1,3-bis(diisopropylphosphino)propane (dippp).

The complexes of the invention are prepared by nucleophilic cleavage of 2- methallylpalladium chloride dimer with sodium methoxide in the presence of two equivalents of the phosphine ligand $R_1R_2P(CH_2)_nPR_3R_4$ and crystallization from a solvent solution at low temperature. For convenience, the complex can also be generated in situ by reaction of a palladium derivative such as $PdCl_2$ or $Pd(OAc)_2$ with two equivalents of the phosphine ligand under the reducing carbonylation conditions.

The invention will be illustrated by the following nonlimiting examples.

EXAMPLE 1

Preparation of the complex catalyst $(dippp)_2Pd$ 2 ml of 1.54M methanol solution of NaOH was added to a suspension of 515 mg (2.6 mmol) of 2-methallylpalladium chloride dimer in 15 ml of methanol under nitrogen. The palladium complex dissolved and 35 ml of methanol was added to the solution, followed by a solution of 1.436 g (5.2 mmol) of dippp in 17 ml of toluene. After stirring at room temperature for 24 hrs, the solution was filtered and the solvent evaporated under vacuum to yield $(dippp)_2Pd$ as an oil, which was crystallized from a saturated solution in pentane at $-30°$ C. $^{31}P[^1H]NMR$ (toluene-$d_8$); $\delta 1.0$ (s, 1P), 45.3 (t, J=84 Hz, 1 P), 21.4 (d, J=84 Hz, 2 P).

EXAMPLE 2

Preparation of benzaldehyde

The complex $(dippp)_2Pd$ was generated in situ by reaction of dippp with $Pd(OAc)_2$. A 90 ml glass pressure tube was charged in a nitrogen dry box with a solution containing 52 mg of $Pd(OAc)_2$, 125 mg of dippp and 0.91 ml of chlorobenzene in 3 ml of dry DMF. After stirring the solution at 25° C. for 1 hr, 3.06 g of sodium formate was added and the mixture was charged with 80 psi of CO and heated with stirring at 150° C. for 18 hrs. After cooling to room temperature, the gas was slowly released by bubbling it through an aqueous solution of BaO, forming a precipitate of $BaCO_3$ which was isolated by filtration and vacuum dried to yield 1.715 g, corresponding to a quantitative reaction of chlorobenzene. The reaction mixture was poured into 50 ml of water and extracted with ether. The ether extract was washed with water, dried over $Na_2SO_4$ and the solvent removed under vacuum. $^1H$ NMR and IR of the residue show that benzaldehyde was obtained in 90% yield.

EXAMPLE 3

Preparation of benzaldehyde

Example 2 was repeated, but the complex $(dippp)_2Pd$ of Example 1 was used as catalyst instead of a mixture of $Pd(OAc)_2$+dippp. Benzaldehyde was obtained in 90% yield.

EXAMPLE 4

Preparation of p-tolualdehyde.

A 90 ml glass pressure tube was charged in a nitrogen dry box with a solution containing 52 mg of $Pd(OAc)_2$, 125 mg of dippp, 3 ml of DMF and 1.06 ml of p-chlorotoluene. After stirring at room temperature for 1 hr, 1.3 g of sodium formate was added and the mixture was charged with 80 psi CO and heated to 150° C. with stirring for 16 hrs. After cooling to room temperature, the pressure was released and the reaction mixture was poured into icy water. Extraction with ether, followed by drying over $Na_2SO_4$ and solvent removal under vacuum, yielded an oil which was purified by short-path distillation to give p-tolualdehyde in 88% yield as revealed by $^1H$ NMR and IR.

EXAMPLE 5

In the same way as in Example 2, p-methoxychlorobenzene was converted to p-methoxybenzaldehyde (yield: 85%).

Other starting materials and products produced according to the process of the present invention are as follows:

| dSTARTING MATERIAL | PRODUCT |
| --- | --- |
| 4-fluorochlorobenzene | 4-fluorobenzaldehyde |
| 2-chloronaphthalene | 2-naphthaldehyde |
| 4-chlorobiphenyl | 4-formylbiphenyl |
| 3-chloroanisole | 3-methoxybenzaldehyde |
| 4-chloroacetophenone | 4-acetylbenzaldehyde |
| 3,5-dimethylchlorobenzene | 3,5-dimethylbenzaldehyde |
| 4-chlorobenzophenone | 4-formylbenzophenone |
| methyl 3-chlorobenzoate | methyl 3-formylbenzoate |
| methyl 4-chlorobenzenesulfonate | methyl 4-formylbenzenesulfonate |

The invention will now be defined by the following nonlimiting claims.

We claim:

1. A process for the production of an aryl aldehyde of the formula

ArCHO wherein Ar is an unsubstituted carbocyclic aryl or a carbocyclic aryl substituted by one or more radicals selected from the group consisting of alkyl, aryl, F, Cl, CN, OR, COR, $CO_2R$ and $SO_3R$, wherein R is H, alkyl or aryl, which comprises catalytic formylation according to the following reaction scheme $ArCl + CO + HCOOX \rightarrow ArCHO + CO_2 + XCl$ wherein Ar is as defined above and X is a cation, the reaction being carried out at elevated temperature and mild pressure and in the presence of a chelate complex catalyst of the formula $(R^1R^2P(CH_2)_nPR^3R^4)_2Pd$ wherein n is 3 or 4 and $R^1$ to $R^4$ are H, alkyl, cycloalkyl or aryl, at least one of them being alkyl or cycloalkyl.

2. A process according to claim 1, wherein the complex catalyst is generated in situ by reaction of $Pd(OAc)_2$ with two equivalents of the phosphine ligand $R^1R^2P(CH_2)_nPR^3R^4$.

3. A process according to claim 1 wherein $R^1$ to $R^4$ are identical alkyl groups and n is 3.

4. A process according to claim 3 wherein $R^1$ to $R^4$ are isopropyl.

5. A process according claim 1 wherein Ar is unsubstituted phenyl optionally substituted by alkyl or alkoxy.

6. A chelate-stabilized complex of the formula $(R^1R^2P(CH_2)_nPR^3R^4)_2Pd$ wherein n is 3 or 4 and $R^1$ to $R^4$ are H, alkyl, cycloalkyl or aryl, at least one of them being alkyl or cycloalkyl.

7. A chelate complex according to claim 6 wherein n is 3 and $R^1$ to $R^4$ are isopropyl.

8. A process according to claim 1 wherein X is the cation of an alkali or alkaline earth metal.

9. A process in accordance with claim 1, wherein Ar is an unsubstituted carbocyclic aryl or a carbocyclic aryl substituted by one or more radicals selected from the group consisting of alkyl, phenyl, F, Cl, CN, OR, COR, $CO_2R$ and $SO_3R$, wherein R is H, alkyl or phenyl.

10. A process in accordance with claim 1, wherein $R^1$ to $R^4$ are H, alkyl, cycloalkyl or phenyl, at least one of them being alkyl or cycloalkyl.

11. A process in accordance with claim 1, wherein $R^1$ to $R^4$ are H, alkyl, cycloalkyl, at least one of them being alkyl or cycloalkyl.

12. A process in accordance with claim 9, wherein $R^1$ to $R^4$ are H, alkyl, cycloalkyl or phenyl, at least one of them being alkyl or cycloalkyl.

13. A process in accordance with claim 9, wherein $R^1$ to $R^4$ are H, alkyl, cycloalkyl, at least one of them being alkyl or cycloalkyl.

14. A process in accordance with claim 9, wherein X is the cation of an alkali or alkaline earth metal.

15. A process in accordance with claim 10, wherein X is the cation of an alkali or alkaline earth metal.

16. A process in accordance with claim 11, wherein X is the cation of an alkali or alkaline earth metal.

17. A process in accordance with claim 12, wherein X is the cation of an alkali or alkaline earth metal.

18. A process in accordance with claim 13, wherein X is the cation of an alkali or alkaline earth metal.

19. A chelate complex according to claim 6, wherein $R^1$ to $R^4$ are H, alkyl, cycloalkyl or phenyl, at least one of them being alkyl or cycloalkyl.

20. A chelate complex according to claim 6, wherein $R^1$ to $R^4$ are H, alkyl, cycloalkyl, at least one of them being alkyl or cycloalkyl.

* * * * *